(12) United States Patent
Tinker et al.

(10) Patent No.: US 6,423,199 B1
(45) Date of Patent: Jul. 23, 2002

(54) ELECTROCHEMICAL ION EXCHANGE USING CARBOLLIDE SYSTEMS

(75) Inventors: Nigel Dennis Tinker, Warrington; James Darcy McKinney, Preston; Simon James Richards, Newcastle-upon-Tyne, all of (GB)

(73) Assignee: British Nuclear Fuels plc, Cheshire (GB)

( * ) Notice: Subject to any disclaimer, the term of this patent is extended or adjusted under 35 U.S.C. 154(b) by 0 days.

(21) Appl. No.: 09/462,857

(22) PCT Filed: Jul. 16, 1998

(86) PCT No.: PCT/GB98/01923

§ 371 (c)(1),
(2), (4) Date: Apr. 10, 2000

(87) PCT Pub. No.: WO99/03582

PCT Pub. Date: Jan. 28, 1999

(30) Foreign Application Priority Data

Jul. 17, 1997 (GB) .............................................. 9715004

(51) Int. Cl.[7] .......................... B01D 61/48; C02F 1/469
(52) U.S. Cl. ....................... 204/536; 204/551; 204/632; 204/647; 556/7; 556/140; 423/2; 588/204
(58) Field of Search ................................. 204/536, 551, 204/632, 647; 556/7, 140; 423/2; 588/204

(56) References Cited

U.S. PATENT DOCUMENTS

| | | | |
|---|---|---|---|
| 5,584,981 A | * 12/1996 | Turner et al. | ................ 204/536 |
| 5,603,074 A | 2/1997 | Miller et al. | .................... 423/2 |
| 5,631,390 A | 5/1997 | Hurlburt et al. | ................ 556/7 |
| 5,666,641 A | 9/1997 | Abney et al. | .................... 423/2 |

FOREIGN PATENT DOCUMENTS

| | | |
|---|---|---|
| EP | 0 150 602 A2 | 8/1985 |
| SU | 1432953 A1 | 6/1994 |
| SU | 1589858 A1 | 7/1994 |
| SU | 1603552 A1 | 7/1994 |
| WO | WO 96/33132 | 10/1996 |

OTHER PUBLICATIONS

Balaich, et al., "Synthesis of cobalt dicarbollide derivatives for addition and condensation polymerization," 211th ACS National Meeting, American Chemical Society, (Mar. 24–28, 1996).

Churchill et al., Technical Report No. 15, "Preparation of Crystallographic Characterization of the $[B_9C_2H_{11} \cdot CoB_8C_2H_{10} \cdot CoB8C_2H_{10} \cdot CoB_9C_2H_{11}{}^{3-}]$ Anion: A System with Four Fused Icosahedra," Prepared for publication in *Journal of the American Chemical Society*, 1–8 (Mar. 26, 1970).

Francis et al., Technical Report No. 20, "Synthesis and Properties of Cobalt Complexes Containing the Bidentate π–Bonding $B_8C_2H_{10}{}^{-4}$ Ligand," Prepared for publication in *Inorganic Chemistry*, 1–16 (Aug. 3, 1970). No month.

Fryberger et al., "Radioactive waste treatment: Russian/U.S. partnership in R and D," *Technol. Programs Radioact. Waste Manage. Environ. Restor.*, (1)1: 125–127 (1994). (Abstract).

Heying et al., "A New Series of Organoboranes. III. Some Reactions of 1,2–Dicarbaclovodecarborane (12) and its Derivatives," *Inorganic Chemistry*, (2)6: 1097–1105 (Dec. 1963).

(List continued on next page.)

*Primary Examiner*—Arun S. Phasge
(74) *Attorney, Agent, or Firm*—Myers Bigel Sibley & Sajovec

(57) ABSTRACT

An electrochemical ion exchange cell comprises a metal carbollide as ion exchange material. The carbollide is preferably a polynuclear cobalt dicarbollide and is typically substituted by chlorine. Also novel are polynuclear metal carbollides comprising a substituted carbollide cage, as well as metal carbollides comprising a carbollide cage substituted by a moiety having a —COOH or —SH group.

30 Claims, 4 Drawing Sheets

OTHER PUBLICATIONS

Hurlburt et al., "New Synthetic Routes to B–Halogenated Derivatives of Cobalt Dicarbollide," *Inorganic Chemistry*, (34)21: 5215–5219 (1995). No month.

Matel et al., "B–Halogen Derivatives of the BIS(1,2–Dicarbollyl)Cobalt(III) Anion," *Polyhedron*, (1)6: 511–519 (1982). No month.

Miller, et al., "New routes to C– substituted derivatives of cobalt dicarbollide," 211th ACS National Meeting, American Chemical Society, (Mar. 24–28, 1996). (Abstract). No month.

Simunicova et al., "Isotachophoretic determination of chloroderivatives of cobaltocarborane without the use of reference analytes," *J. Chromatogr*, (390)1: 121–132 (1987). (Abstract).

Steckle Jr. et al., "Cobalt Dicarbollide Containing Polymer Resins for Cesium and Strontium Uptake," *CDC in Polymer Resins*, Los Alamos National Laboratory, Polymer and Coatings Group: 507–508 (Nov. 25, 1996).

"The First Industrial HLW Partitioning Installation in Russia is Operational," *Post–Soviet Nuclear & Defense Monitor*, Exchange/Monitor Publications, Inc.: 10 (Aug. 29, 1996).

Turner, et al., "Electrical Processes for the Treatment of Medium Active Liquid Wastes Final Report Jan. 1983–Apr. 1985," (1985).

Turner, et al., "The EIX Process for Radioactive Waste Treatment," AEA Technology: 1–10 (Jan. 8, 1996).

Volkov, O. V. et al., "Synthesis and properties of polynuclear cobalt (III) complexes with dicarbollide (2–)– and dicarbacanastide (4–)– anions, " *Izvestiya Akademii nauk*, Chemistry Series, (4): 977–983 (1996). No month.

* cited by examiner

ELECTROCHEMICAL ION EXCHANGE USING CARBOLLIDE SYSTEMS

This application is a 371 of PCT/GB98/01923 filed Jul. 17, 1998.

BACKGROUND OF THE INVENTION

1. Field of the Invention

The present invention relates to the use of carbollide systems for cation removal from aqueous media using electrochemical ion exchange. More particularly, it relates to novel cobalt carbollide materials useful in electrochemical ion exchange cells.

An exemplary electrochemical ion exchange ("EIX") cell comprises two working electrodes positioned on either side of a chamber, each having an unflattened expanded mesh counter electrode in close proximity to its surface. The working electrode surfaces are exposed to, for example, a waste stream. FIG. 1 shows such an EIX flow cell. In FIG. 1, each working electrode 1 is embedded in an ion exchange material 2 (typically a resin) and has a mesh counter electrode 3 juxtaposed to its surface. The arrows a and b show where the waste stream enters and leaves the cell.

In use. therefore, an aqueous medium is passed through the chamber. A negative potential is applied to the weak acid cation exchanger causing rapid adsorption of ions to the cathode (working electrode) from the solution. The electric field across the ion exchange material layer between the current feeder and counter electrode encourages this cation migration.

For eluting the cations, a flush solution is passed through the chamber. Upon polarity reversal, the adsorbed ions can then be eluted into a limited volume of water to give a concentrated product. Elution is caused by the reversed electric field oxidising water at the current feeder of the working electrode, and thereby generating protons which displace the cations. The adsorption capacity of EIX electrodes can be used many times over under external electrical control.

Electrochemical ion exchange has been found to be a robust and effective process for active liquid wastes treatment, and to be capable of achieving high decontamination, volume reduction factors and a low energy consumption.

2. Brief Description of the Related Art

Electrochemical Cells

An EIX system has previously been developed by Turner et al. which allows ionic material to be adsorbed and eluted electrically by polarity reversal with great efficiency. Decontamination of a factor of 2000 has been observed for caesium removal with up to 75% loading of ion exchanger at flow rates of 8 bed volumes per hour. Unfortunately. the complexing agent used was not mentioned by Turner et al. but the context in which it was discussed would suggest it was an organic ion exchanger. Inorganic ion exchangers have also shown selectivity for cations.

Separated electrochemical cells have also been developed for removing ions such as strontium and caesium from aqueous solution. The cell consists of two compartments, each containing one electrode and separated by an anion selective membrane. Both electrodes may be working electrodes, or one may be acting as a counter electrode.

Platinized titanium has been successfully used as the working electrode due to its corrosion resistance. However, this material catalyses hydrogen gas production. Cheaper materials of unknown identity which are in development are claimed to be five times more cost effective.

Boranes and Carboranes

Compounds consisting entirely of boron and hydrogen are termed boranes. Boranes exist as cages which can be closo, nido, arachno, or hypho. Closo is a fully closed cage, nido has the most electron deficient boron removed, and arachno has the two most electron deficient borons removed.

Boranes containing carbon are termed either carbaboranes or carboranes. Carboranes which have undergone degradation are usually referred to as carbollide ions. Ortho-carborane (7,8-dicarborane, $C_2B_{10}H_{12}$) can be used to prepare the ortho-dicarbollide ion ($C_2B_9H_{11}$), also referred to as 7,8-dicarbollide. This ion can easily be stored as nido-dicarborane ($C_2B_9H_{12}$). The carbollides of many metals are known. These metals include first row transition metals such as iron and nickel, for example, and also f-block metals.

Cobalt Bis-7,8-dicarbollide (CDC)

Structure: $[(C_2B_9H_{11})_2Co]^-$. Registry Number: 11078-84-5.

IUPAC Name: Cobaltate(1-), bis [(7,8,9,10,11-.eta)-undecahydro-7,8-dicarba-undecaborato(2-)]-(9CI).

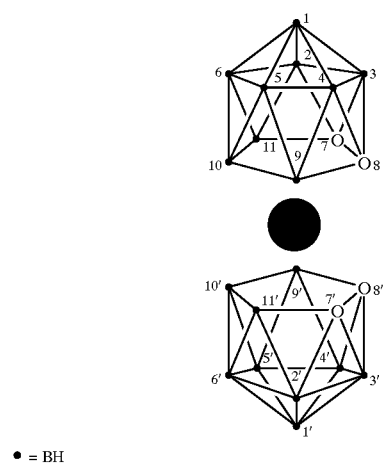

● = BH
○ = CH

CDC is a carborane product comprising cobalt (III) as a metal atom centre surrounded by two hemisphere cages of carboranes. The carborane ligands are of the nido structure variety.

CDC has been researched in detail in relation to caesium and strontium removal from aqueous solution. Since chlorinated cobalt bisdicarbollide is hydrophobic by nature, it allows the extraction of caesium and strontium ions by solvent extraction techniques. This process mainly concerns the use of nitrobenzene, which is toxic, and polyethylene glycol. As of August 1996, 26 cubic metres of high level waste has been reprocessed at the Mayak Production Association (PA) at Chelyabinsk[2] using chlorinated CDC. The recovery degree for both strontium and caesium is over 99%. This work is being carried out by a joint U.S.-Russian research and development project at the Khlopin Radium Institute in St. Petersburg[3].

A paper has been published on the attachment of cobalt bisdicarbollide to polymer resins[12] using butyl lithium with the polymers polystyrene and polybenzimidazole. There is also a paper[1] which describes putting organic chains on to the cobalt bisdicarbollide in an attempt to cause polymerisation by condensation reactions. The products were proposed for use in a liquid-liquid solvent extraction system. and also as the active sites of cation exchange on grafted polymer supports.

5,6,10-Hexachloro Cobalt bis-7,8-dicarbollide

Structure: $[(C_2B_9H_8Cl_3)_2Co]^-$. Registry Number: 107105-38-4.

IUPAC Name: Cobaltate(1-), bis[(7,8,9,10,11-eta.)-trichlorooctahydro-7,8-dicarba-undecaborata(2-)] (9CI).

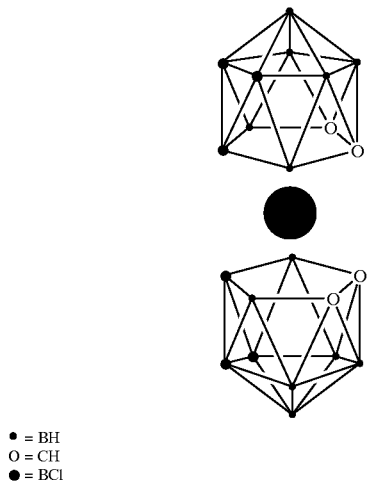

• = BH
○ = CH
● = BCl

This hexachloro CDC derivative has been used in the solvent extraction of caesium into nitrobenzene at the Khlopin Institute as discussed earlier, as well as in the separation and detection of different chloro derivatives of cobalt dicarbollide by isotachophoretic determination[6].

The chlorinated cobalt bisdicarbollide can be prepared by several methods[7]. The hexachlorinated CDC can be prepared by:

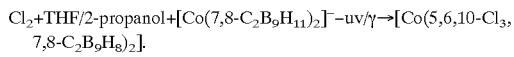

Cl$_2$+THF/2-propanol+[Co(7,8-C$_2$B$_9$H$_{11}$)$_2$]$^-$-uv/γ→[Co(5,6,10-Cl$_3$, 7,8-C$_2$B$_9$H$_8$)$_2$].

Three patent documents discuss chlorinated CDC derivatives used in a solvent extraction system[5].

Cobalt Dicarbollide Trimer

Structure: $[Co_3(C_2B_9H_{11})_2(C_2B_8H_{10})_2]^{3-}$. Registry Number: 59200-84-9.

IUPAC Name: Cobaltate(3-), bis[.mu.-[.eta.5-decahydrodicarbadecaborato(4-)]]bis [7,8,9,10,11-.eta.)-undecahydro-7,8-dicarbaundecaborato(2-)]tri-(9CI).

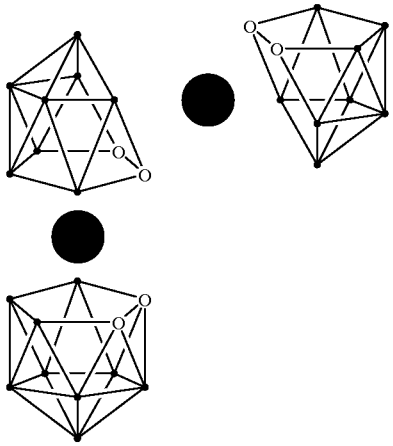

• = BH
○ = CH

In metal carbollide chemistry, the term "trimer" refers to a complex containing 3 metal atoms (Co (III) in the illustrated case) in a multilayer "sandwich" of four carbollide ions. Alternatively, such a trimer may be referred to as a trinuclear complex.

The trinuclear CDC complex is known only as a research curiosity. A recent paper by Volkov et al[10] describes the production of several oligomers (polynuclear complexes). Earlier publications relate to the preparation and spectra characterisation of the trimer[8] and crystallographic characterisation[9] of its anion.

EP-A-0 150 602 discloses metal carbollides and their use as charge transfer mediators in enzyme based electrochemical assay systems.

WO-A-96/331132 discloses processes for extracting cesium and strontium ions from nuclear waste using substituted metal dicarbollides as extraction agents.

SUMMARY OF THE INVENTION

The present invention provides the use as an EIX ion exchange material in a flow through electrochemical cell of a metal carbollide and especially of cobalt carbollides. The invention also provides electrochemical ion exchange cells characterised in that the ion exchange material is a metal carbollide. Preferably the EIX cell comprises:

a housing having a chamber defined therein;

a working electrode disposed within the chamber and associated with the metal carbollide ion exchange material; and a counter electrode juxtaposed to an exposed surface of the ion exchange material.

The metal carbollide normally contains a dicarbollide and more preferably the carbollide ions are exclusively dicarbollide ions. The dicarbollide is usually ortho-dicarbollide.

Another product of the invention is a metal carbollide which comprises a carbollide cage substituted by an organic moiety selected from carboxylic acids and thiols. The carbollide cage may be substituted by a halogen, especially chlorine, which provides a product of good stability. Alternatively, the carbollide cage may be substituted by an organic moiety having a functional group. The functional group may be a group which can be used to bond the carbollide to a metal (especially a working electrode) or a functionality useful for grafting the carbollide onto a polymer. A further class of substituents are those functional

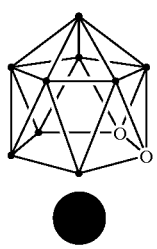

groups useful for interconnecting carbollide cages, suitably to form a polymer. More generally, substituents may be selected, for example empirically, to modify the properties of the polynuclear carbollide. Further aspects and embodiments of the invention will be apparent from the following description and claims.

DESCRIPTION OF THE PREFERRED EMBODIMENTS

Figure 1:
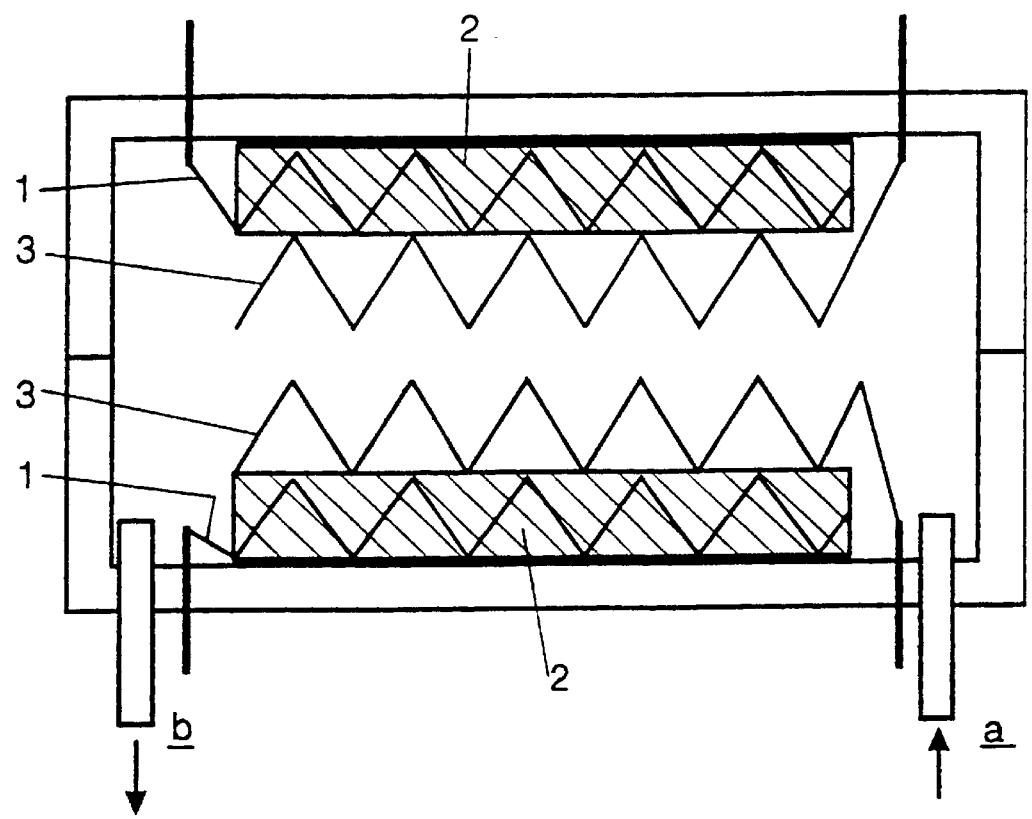
FIG. 1 is a diagrammatic illustration of an EIX flow cell of conventional structure in which a metal carbollide may be used as ion exchange material.

The invention relates to EIX cells which contain a metal carbollide ion exchanger. The metal is usually cobalt and the carbollide moieties are normally dicarbollide, especially ortho-dicarbollide.

The carbollide ions, often referred to as carbollide cages, may each independently be substituted by one or more substituents, in particular selected from halogen, especially chlorine, and organic moieties. The substituents may be chosen to modify the properties of the carbollide; for example halogenated and, especially, chlorinated carbollides have good stability. Trichlorocarbollide is a particularly preferred carbollide ion, especially trichloro dicarbollide and most especially 5,6,10-trichloro-7,8-dicarbollide. As the organic moieties may be mentioned carboxylic acids and thiols coupled to the working electrode, as described in more detail below. These functional groups (carboxyl and thiol) may be attached to their associated carbollide cage via an alkyl chain optionally attached to an aromatic ring. The alkyl chains of such moieties may contain. for example from 1 to 20, carbon atoms, and optionally contain an ether linkage. More usually, the alkyl chains of such moieties contain at least 3 carbon atoms. Exemplary organic moieties are carboxyalkyl or alkanethiol residues.

The invention therefore includes EIX cells wherein the organic moiety is attached to a carbon site of the carbollide cage to which it is bonded and is of the formula

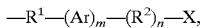

—R$^1$—(Ar)$_m$—(R$^2$)$_n$—X, wherein Ar is an aromatic group, m and n are each independently 0 or 1, R$^1$ and R$^2$ are each independently an alkylene group and X is COOH or SH coupled to the working electrode. The total number of in-chain alkylenic carbon atoms is suitably at least 3 and optionally no more than 20. The alkylene group(s) may each independently be interrupted by an ether linkage. Ar is preferably phenyl, which may be inertly substituted.

Any organic substituent groups of the metal carbollide of a cell of the invention are bonded to a carbon site of the carbollide cage, with the exception of amines which may bond to a boron site by the use of a boron-nitrogen bond.

The metal carbollide may desirably be coupled directly to the working electrode, whether by covalent bonds or otherwise, in order to prevent or reduce leaching of the carbollide into liquid in the cell.

In one class of cells, therefore, one or more of the carbollide ions of the metal carbollide are substituted with moieties containing a carboxyl group for binding to, for example, an electrode of steel or titanium or other non-inert metal. In another class of embodiments one or more of the carbollide ions of the metal carbollide are substituted with moieties containing a thiol group for binding to, for example, a platinum or gold electrode. Thus. metal carbollides provided with an SH group may be bound to a gold or platinum electrode, for example by a technique already known per se. Alternatively, metal carbollides provided with a —COOH group (or other reactive carbonyl-containing function) are suitable for binding to most other metals, such as steel or titanium, for example. In a second class of cells the metal carbollide is coupled to a resin (e.g. to help resist leaching of the metal carbollide).

Additionally or alternatively the metal carbollide may be in the form of an oligomer or a polymer comprising links (e.g. organic bridging groups) between carbollide ions of adjacent complexes in order to increase resistance to leaching.

The metal carbollide complex may in principle contain any desired number of carbollide cages. Thus it may be a "monomer" (i.e. a mononuclear complex containing one metal atom associated with the two carbollide ions) a "dimer" (i.e. a dinuclear complex containing two metal atoms and three carbollide ions), or a "trimer" (i.e. a trinuclear complex containing three metal atoms and four carbollide ions).

The EIX cell is preferably a flow cell. i.e. a cell comprising a liquid inlet and a liquid outlet, the inlet and the outlet being located for liquid to flow across the ion exchange material.

The EIX cells of the invention normally comprise two opposed working electrodes.

The invention includes in another aspect cation exchanger electrodes comprising a working electrode associated with a metal carbollide, for example as described more particularly above in relation to the cell of the invention. (The term "working electrode" is used to refer to the current feeder. which is typically a metal wire or metal mesh. whereas the working electrode with the ion exchanger attached is a "cation exchanger electrode").

Further provided by the invention is a process for removing cations from solution by electrochemical ion exchange characterised in that the ion exchange material is a metal carbollide. The process of the invention preferably uses an EIX flow cell as described above. The cations are usually metal cations and in some preferred embodiments comprise strontium or caesium ions, or both.

More particularly, the invention provides an EIX process for removing from an aqueous medium dissolved cations extractable using a metal carbollide, especially in the decontamination of aqueous media containing strontium and/or caesium ions. which process comprises:

providing an EIX flow cell having a cathode comprising a metal carbollide as ion exchange material;

applying a negative potential to the cathode;

passing the aqueous medium through the flow cell; then passing a flush liquid into or through the flow cell and, whilst the flush liquid is in the flow cell, applying a positive potential to the cathode to cause adsorbed cations to elute into the flush liquid.

Cations removable by the above process include strontium, caesium, barium, cerium, europium and uranium. Conditions suitable for removing a particular one of these ions may be determined empirically.

The invention yet further includes a polynuclear metal carbollide, that is one containing at least two metal atoms complexed by at least three carbollide cages (i.e. a 2-mer or greater oligomer), characterised in that it comprises a substituted carbollide cage.

The carbollide cages of the substituted polynuclear complexes are normally dicarbollides, especially ortho-carbollides. The metal is preferably cobalt. In one class of complexes all the carbollide cages are substituted, optionally by the same substituent(s) at the same site(s).

Preferably, the polynuclear complexes are trinuclear.

A particularly preferred class of substituted metal carbollides are halogenated. normally at a boron site. More than one boron may be halogenated. A preferred halogen is chlorine. Bromine may be mentioned as an alternative halogen to chlorine. Preferably, the carbollide cages are substituted by three halogen atoms, each preferably on a boron atom adjacent another halogenated boron atom.

Particularly preferred halogenated metal carbollides are chlorinated trinuclear complexes, of which may be mentioned in particular the dodecachloro trimer [$C_2B_9H_8Cl_3$—Co—$C_2B_8H_7Cl_3$—Co—$C_2B_9H_8Cl_3$]$^{3-}$ and tretrachlorinated CDC trimer.

Another preferred class of substituted metal carbollides consists of those which are substituted by an organic moiety. The organic moieties desirably have a functional group useful for a purpose such as, for example, one or more of the following:

(i) coupling the carbollide to a metal, especially the working electrode, for which purpose thiol or carboxyl functionalities are useful;

(ii) grafting onto polymers, for which purpose reactive groups (e.g. Li$^+$) are suitable which cause nucleophilic attack, to enable nucleophilic substitution onto halogenated polymers.

(iii) linking carbollide cages together, for which purpose groups (e.g. OH or COOH) reactive towards condensation and addition polymerisation may be useful.

Preferred organic moieties are selected from carboxylic acids and thiols. The acids may be in the form of a reactive derivative thereof. The organically substituted metal carbollides may be as described above in more detail in relation to the EIX cells of the invention. The invention therefore includes such carbollides in which the organic moiety is attached to a carbon site of the carbollide cage to which it is bonded and is of the formula

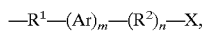

wherein Ar is an aromatic group (e.g. phenyl), m and n are each independently 0 or 1, R$^1$ and R$^2$ are each independently an alkylene group optionally interrupted by an ether linkage and X is COOH or SH, the COOH optionally being in the form of a reactive derivative thereof.

Metal carbollides which are both C-substituted by an organic moiety and B-substituted by a halogen are included in the invention.

Preparation of the Metal Carbollide

Metal dicarbollides and their preparation are known. In an exemplary method for making cobalt bisdicarbollide, nido carborane and a cobalt (II) salt. e.g. cobalt (II) chloride, are reacted in aqueous alkali, such as 10M NaOH, for example. The reagents are in practice reacted at elevated temperature, for example under reflux. The resultant cobalt bisdicarbollide may be isolated using chromatography. Analogous procedures may be used to form other metal carbollides.

Cobalt dicarbollide oligomers may be prepared as described by Volkov O. V. et al[10], for example. In a procedure for making the trimer [$B_9C_2H_{11}$—Co—$B_8C_2H_{10}$—Co—$B_8C_2H_{10}$—C0—$B_9C_2H_{11}$]$^{3-}$, ortho-carborane ($C_2B_{10}H_{12}$) is reacted, typically under reflux, with base (e.g. ethanolic KOH) to form a carbollide salt. The carbollide salt is then reacted with a cobalt (II) salt in a basic medium (e.g. aqueous NaOH), typically under reflux, to form the trimer. A preferred procedure is:

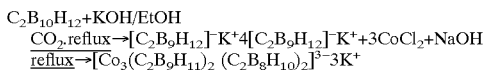

(The oxidation of Co(II) to Co(III) in the second reaction is believed to result from a disproportionation reaction: 3 Co(II)→2 Co(III)+Co(0)).

Preparation of Metal Halocarbollides

Metal halocarbollides may be made, for example, by halogenating the corresponding metal dicarbollide, and then, if necessary, oligomerising the metal di(halocarbollide). Suitable procedures are described by Hurlburt, P.K. et al[7] and Matel L. et al[14]. In one procedure, the metal dicarbollide. e.g. 7,8-$C_2B_9H_{11}$—Co-7,8-$C_2B_9H_{11}$, is reacted with, in particular, chlorine in the presence of an inert organic solvent (e.g. THF and/or an alcohol) and preferably under ultraviolet and/or gamma radiation. One technique is described by the following reaction scheme:

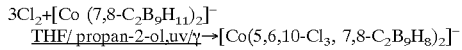

The resultant cobalt (or other metal) di(halocarbollide) may be formed into the corresponding "trimer" [$B_9C_2H_8Cl_3$—Co—$B_8C_2H_7Cl_3$—Co—$B_8C_2H_7Cl_3$—Co—$B_9C_2H_8Cl_3$]$^{3-}$. A preferred procedure is:

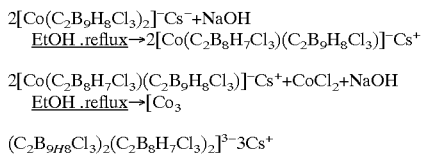

As an alternative to forming halogenated polynuclear complexes by halogenating a mononuclear complex which is then converted to a polynuclear complex, a non-halogenated polynuclear complex may be halogenated.

Substitution of metal carbollides with organic side chains

Organic side chains may be attached to metal carbollides using known techniques, for example. Suitable techniques are taught by Miller R. L. et al[13] and Steckle W. P. Jr. et al[12]. In general terms, these procedures involve contacting a metallated deprotonated carbollide such as lithium carbollide (which is a nucleophilic species) with an organic compound containing a leaving group, to effect nucleophilic substitution. Chlorine is the usual leaving group, or another halogen. The lithiated carbollide species may be made by deprotonating the corresponding metal carbollide, typically to form stable and isolable lithiated species. In practice, the reaction is performed in an inert organic solvent, for example tetrahydrofuran which must be free from any water.

The invention therefore includes a method of making an organically substituted metal carbollide of the invention, comprising reacting a metal carbollide having a metallated carbollide cage with a compound of the formula R$^3$-Lg, wherein R$^3$ is the organic substituent and Lg is a leaving group.

Alkane thiol derivatives and alkaryl thiol derivatives, therefore, may be formed by contacting the metal carbollide with a strong base such as [11]BuLi and reacting the resultant lithium salt with a chloroalkanethiol or a chloroalkaryl thiol (i.e. $Cl(CH_2)_pSH$ or $Cl(CH_2)_pC_6H_4SH$, where p is in principle any integer (but is usually between 3 and 20) and the phenyl residue $C_6H_4$ may be replaced by another aromatic residue containing for example from 6 to 12 ring atoms).

Binding of Substituted Metal Carbollides to Electrodes

Organically substituted CDCs can be bound to electrodes using one of the following methods, for example.

Thiol-substituted CDCs may be dissolved in a suitable solvent (eg ethanol) and gold or platinum metal, for example, is submerged in the solution. The reaction time may range from several hours to several days, depending upon the thiol. No heat is necessary.

In the case of carboxyl-substituted CDCs, the metal surface (typically titanium or stainless steel) is activated in concentrated HCl (eg 6 Molar). The carboxyl-substituted CDC is then dissolved in a suitable solvent (eg ethanol) and the activated metal is submerged in the solution, The reaction time may range from several hours to several days, depending upon the carboxylic acid. No heat is necessary.

Bonding of Substituted Metal Carbollides to Polymers

Metal carbollides may be grafted onto polymer supports by a nucleophilic substitution reaction using a lithiated carbollide (i.e. carbollide cage anion) or by substituting a carbollide with an organic side chain having a functional group reactive towards condensation or addition polymerisation.

For example, Steckle W. P. Jr. et al[12] teach that lithiated carbollide may be reacted with chloromethyl polystyrene or with polybenzimidazale (PBI) onto which epichlorohydrin was grafted to provide a chlorine leaving group. Grafting of epichlorohydrin onto the PBI involves opening of an epoxide to form a hydroxyl group, which was protected using hexamethyldisilazane prior to reaction with lithiated carbollide.

Techniques similar to those used to graft metal carbollides onto polymers may be used to interconnect carbollide cages so as to form a polymer (e.g. an oligomer). Thus. organic side chains bearing reactive functional groups may be reacted together or a metallated carbollide cage may be reacted with an organic side chain substituted with chlorine or another leaving group.

The invention is further illustrated by the following examples.

EXAMPLE 1

Preparation of Nido-Carborane

Potassium hydroxide (5 g, 89 mmol) was dissolved in ethanol (100 cm$^3$) and added to a 3 neck round bottom flask (250 cm$^3$) with reflux condenser, magnetic stirrer, and nitrogen inlet. ortho carborane (4.14 g, 28.7 mmol) was added and the solution was stirred for one hour. This was then refluxed for four hours and then carbon dioxide was allowed to bubble through the solution for five minutes. The resultant precipitate was filtered by suction and the filtrate collected. The filtrate was evaporated to dryness in vacuo and diethyl ether was added to the dried product. This was filtered by vacuum again, dried in vacuo, and then stored in a vacuum desiccator.

EXAMPLE 2

Preparation of Cobalt bisdicarbollide from Nido Carborane

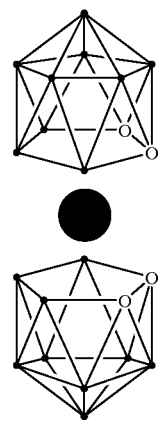

● = BH
O = CH

10 M sodium hydroxide (100 cm$^3$) was added to a 2 neck round bottom flask (250 cm$^3$) with nitrogen inlet, magnetic stirrer, and reflux condenser. This was heated to reflux and nido carborane (2.05 g, 15.4 mmol) was added slowly, followed by hexahydrated cobalt chloride (2.00 g, 8.5 mmol) in 10 M sodium hydroxide (50 cm$^3$). This was refluxed for 30 minutes and was then added to water (150 cm$^3$). The resultant solution was extracted into diethyl ether (1000 cm$^3$) and evaporated to dryness in vacuo. The product was then treated to column chromatography in a 2:1 chloroform/acetonitrile mix using silica gel. Two bands were obtained which were yellow and red respectively. The bands were evaporated to dryness in vacuo and stored in a vacuum dessicator to give a yellow and red solid. The yellow solid is the desired product.

EXAMPLE 3

Preparation of 8,9,12 Hexachloro CDC

The preparation is carried out according to the procedure of Matel et al[14]. Gaseous chlorine is bubbled through a solution of 4.57 g (10 mmol) of caesium cobalt bisdicarbollide in a mixture of ethanol-tetrachloromethane (70:30 v/v) under cooling. The reaction is stopped after the absorption of 4.61 g (~60 mmol). White crystals of caesium chloride are removed by filtration and, after evaporation of the solvent, the product is purified and isolated by gel chromatography and then recrystallised from the ethanol-acetone-water (50:20:30 v/v) mixture. The yield is typically ~4.2 g (65%).

EXAMPLE 4

Preparation of CDC Trimer

Potassium hydroxide (2.05 g) is dissolved in ethanol (40 cm$^3$) and placed in a 3 neck round bottom flask (100 cm$^3$) with reflux condenser magnetic stirrer, and nitrogen inlet. The ortho carborane (2.10 g, 14.6 mmol) was added and the solution was stirred vigorously for one hour. Solution was then refluxed until hydrogen gas ceased to evolve (4 hours).

Carbon dioxide gas was then bubbled through the solution to neutralise the solution to pH 7. The resultant solution was filtered by suction and washed with ethanol (50 cm$^3$) to remove potassium carbonate. The filtrate was removed in vacuo leaving a creamy liquid which was stored in a vacuum desiccator to leave an off white precipitate (2.40 g, 13.9 mmol). This precipitate (2.40 g, 13.9 mmol) was dissolved in 40% sodium hydroxide solution (100 cm$^3$) and added to a round bottom flask (100 cm$^3$) with hexahydrated cobalt chloride (2.05 g, 8.16 mmol). The solution was refluxed for 6 hours with stirring in an inert atmosphere. This was then extracted into diethyl ether (1000 cm$^3$). This was dried in vacuo to leave a dark red oil. A column chromatogram was performed using a 3:1 chloroform/acetonitrile mix in Silica gel. Three bands were obtained. Band 1 was yellow in colour suspected as being starting material. Band 2 was red and in a very small amount. Band 3 was also red and the desired product.

The compound is formed in a solution of very basic pH (10 Molar potassium hydroxide. pH>14), indicating that it is stable in highly alkaline conditions.

EXAMPLE 5

Preparation of Chlorinated CDC Trimer

Hexachloro CDC was purified by column chromatography. Sodium hydroxide (10.00 g) was dissolved in ethanol (100 cm$^3$) and added to a round bottom flask (250 cm ). Purified hexachloro CDC (2.00 g, 3.02 mmol) was added and the solution was brought to reflux with a nitrogen inlet, and magnetic stirrer for four hours. Hexahydrated cobalt chloride (0.65 g, 2.73 mmol) was added to 10% sodium hydroxide in ethanol solution (50 cm$^3$) and this was added to the reaction mixture. This was allowed to reflux for 24 hours. The resultant solution was an intense orange/brown colour. Water (200 cm$^3$) was added to the solution and the ethanol was evaporated off. The solution was extracted into diethyl ether (500 cm$^3$) to leave a red/brown ether layer and a green aqueous layer. The ether layer was dried in vacuo and treated to column chromatography in a 2:1 chloroform/acetonitrile mixture in silica gel yielding four bands. The bands were yellow, brown, green/brown, and dark red in colour respectively. The red band is the desired product.

Results

The fourth band was the chlorinated CDC trimer in a yield of 9% [Found: IR $\nu_{max}$ cm$^-$; 3050 w (sp$^2$ CH), 2974 m (sp$^3$ CH), 2920 m (sp$^3$ CH), 2882 m (sp$^3$ CH), 2572 s (BH), 1472 m, 1387 w, 1101 w, 1026 w, 969 w, 929 w, 873 s, 755 m, 668 w, 502 w, 431 w: $^{11}$B NMR δppm (intensity); −25.7357 s (1), −20.4115 s (4), −4.4389 d(13), 1.8124 d (17), 13.3085 d (4), 24.4639 s (2): $^1$H NMR δppm; 2.1788 s: Mass Spectrum m/z (I %) -ive FAB; 129 (100), 202 (25), 248 (35), 294 (45), 377 (30), 733 (30), 767 (45), 802 (15)].

From the IR analysis, the product seems pure since there is only one B-H absorption peak, also peaks are favourably shown for B-C and C-Cl stretches. The negative FAB analysis seems to indicate that eight chlorines may be missing from the trimer, possibly indicating a tetrachlorinated CDC trimer. However molecules at very large masses may not show up as the entire molecule on the mass spectrometer. Accordingly, the molecule may contain more than 4 chlorine atoms.

The compound is formed in a solution of very basic pH (10 Molar sodium hydroxide, pH>14), indicating that it is stable in highly alkaline conditions.

EXAMPLE 6

Polynuclear CDC Derivative

Sodium hydroxide (30.00 g) was partially dissolved in ethanol (100 cm$^3$) and refluxed for one hour. The sodium hydroxide solution was hot filtered directly into the reaction vessel. Hexachloro CDC (2.00 g, 3.02 mmol) and hexahydrated cobalt chloride (0.65 g, 2.73 mmol) was added and the solution was brought to reflux with a nitrogen inlet, and magnetic stirrer for 24 hours. The resultant solution was an intense brown colour and allowed to cool to room temperature. The ethanol was removed in vacuo and the residue extracted into acetonitrile (4×100 ml). The acetonitrile washings were combined and the solvent removed in vacuo to leave an oily residue. The desired product was isolated using column chromatography using chloroformnacetonitrile (2:1) as the eluants. The bands were yellow, red and brown in colour respectively. The red band was suspected as being the desired product.

Figure 2:
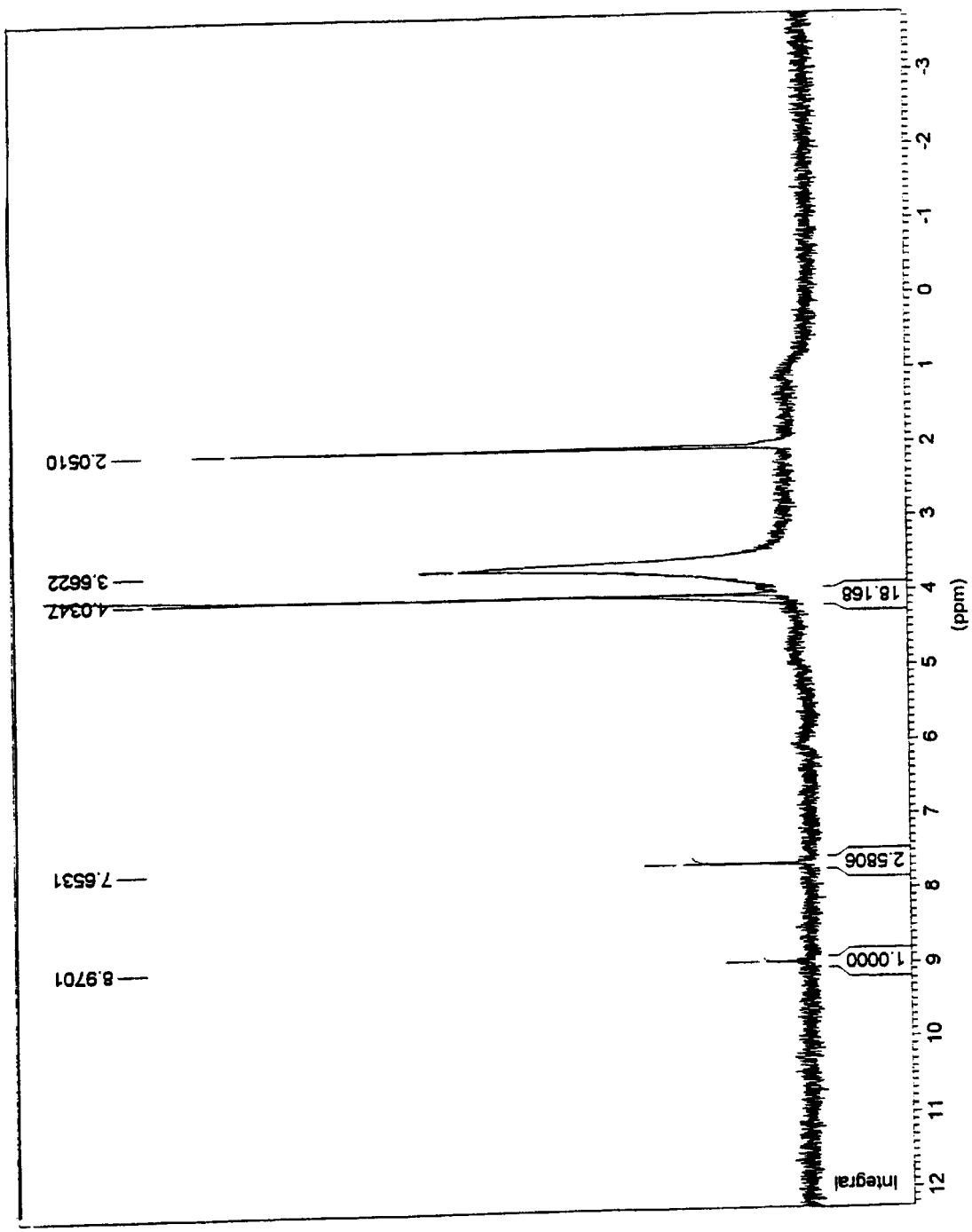
FIG. 2 is an $^1$H NMR spectrum of a polynuclear cobalt carbollide.
Figure 3:
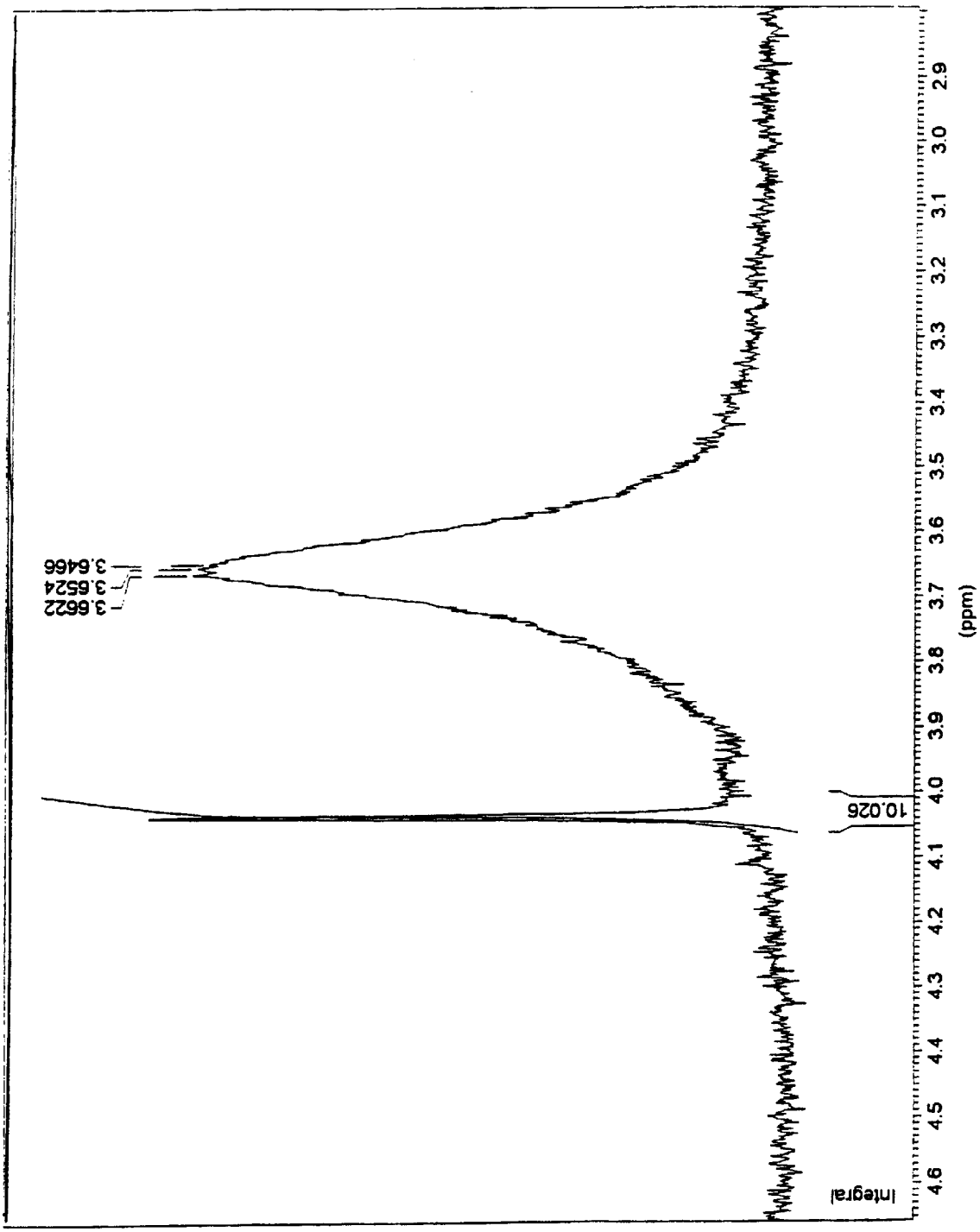
FIG. 3 is a second $^1$H NMR spectrum of the polynuclear cobalt carbollide.
Figure 4:
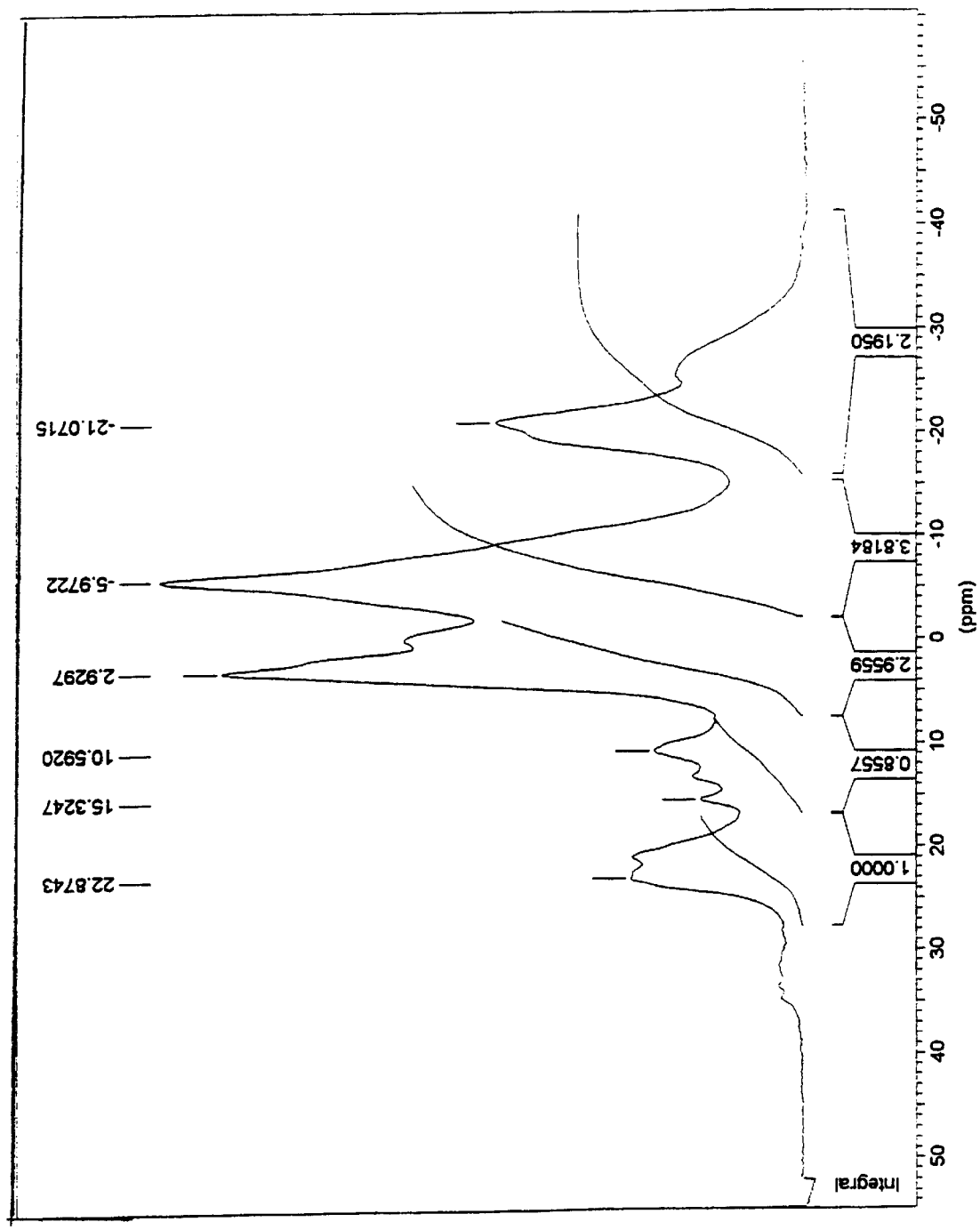
FIG. 4 is a $^{11}$B NMR spectrum of the polynuclear cobalt carbollide.

$^1$H and $^{11}$B NMR spectra of the red product were obtained and are shown in FIGS. 2 to 4. the spectra clearly indicate the presence of a carbollide cage. In the $^1$H NMR one would exect to see two different proton environments relating to the C-H environments in the nido and arachno carbollide cages. In the $^1$H NMR spectra of FIGS. 2 and 3 there is only one visible C-H environment at 4.035 ppm (arachno C-H); the other is thought to be under the water peak at 3.662 ppm. The $^{11}$B NMR spectrum indicates that the product contains a carbollide cage. As the product is red and contains the carbollide, it can be concluded that an oligomeric species has been formed. It would be consistent with the starting materials for the product to be the dodecachloro cobalt carbollide trimer [$C_2B_9H_8Cl_3$—Co—$C_2B_8H_7Cl_3$—Co—$C_2B_8H_7Cl_3$—Co—$C_2B_9H_8Cl_3$]$^{3-}$.

The invention includes a product having the characteristics of a product prepared by reacting hexachloro CDC and hexahydrated cobalt chloride in an alcoholic (eg ethanolic) base (for example NaOH dissolved in ethanol). The reaction is suitably carried out under reflux, for example for about 24 hours. The product may be isolated by removing the alcohol and extracting the residue into acetonitrile, as described above.

The invention also includes a product having the $^1$H and $^{11}$B NMR spectra of FIGS. 2 and 4.

EXAMPLE 7

Hexachloro Cobalt bisdicarbollide Stability in 6 M Nitric Acid

Hexachloro CDC after 0 hrs [Found: UV-VIS λ nm, conc. mols dm$^{-3}$; 307.3 (2.245×10$^{-5}$)$^{11}$B NMR δ ppm (intensity); −24.2145 s (1), −17.6416 d (2), −4.9460 d (2), 3.0404 d (3), 12.5479 s (1)].

Hexachloro CDC after 64 days [Found: UV-VIS λ nm, conc. mols dm$^{-3}$; 304.0 (2.014×10$^{-5}$): $^{11}$B NMR δ ppm (intensity); −24.4680 s (1), −17.6226 d (2), −4.8192 d (2), 3.1672 d (3), 12.2943 s (1)].

The results indicate that the hexachloro cobalt bisdicarbollide is very stable in acidic media such as nitric acid. The UV-VIS analysis has shown no shift in the wavelength of absorbance, but from the Beer-Lambert law, the concentration of the sample has decreased by 10% after 64 days. The $^{11}$B NMR analysis after 64 days has shown minimal changes to the $^{11}$B NMR analysis after 0 hrs. Only one peak from each doublet shifted. The carborane cage geometry is clearly still present and mainly unaffected.

EXAMPLE 8

Leaching Tests

Leaching tests were performed on hexachloro cobalt bisdicarbollide adsorbed into a polymer resin on a steel wire. Two wires were used to help increase the accuracy of the results. Two coated steel wires were placed in 50 cm$^3$ of water for 7 days and analysed by UV-visible spectroscopy for any leaching of the hexachloro CDC into the water. Similar leaching tests were also performed on hexachloro CDC in 6M nitric acid and on CDC dimer in 6M nitric acid.

Results a. Hexachloro CDC in Water

UV-visible analysis of coated wire submerged in water for 7 days showed that a very small amount of hexachloro CDC was found in the solution, ie there was very little leaching. Even this may simply have been loosely bound CDC on the polymer surface since no further leaching was found subsequently. The concentrations observed were:

Wire 1: Concentration of hexachloro CDC in solution 9.186×10$^{-7}$ mol dm$^{-3}$.

Wire 2: Concentration of hexachloro CDC in solution 8.635×10$^{-7}$ mol dm$^{-3}$.

b. Hexachloro CDC in 6M Nitric Acid

After 24 days. there was no observable colour change to the liquid. The concentrations observed were:

Wire 1: Concentration of hexachloro CDC in solution; 2.796×10$^{-5}$ mol dm$^{-3}$.

Wire 2: Concentration of hexachloro CDC in solution: 2.561×10$^{-5}$ mol dm$^{-3}$.

b. CDC Dimer in 6M Nitric Acid

After 21 days, there was no observable colour change to the liquid.

These tests have shown only small amounts of leaching. Therefore showing that CDC systems can beneficially be used in electrochemical ion exchange cells.

REFERENCES

1. Electrical processes for the treatment of medium active liquid wastes: Final report January 1983–April 1985.
   Turner. A D; Bowen, W R; Bridger, N T; Junkinson, A R; Cox, D R.
   Harwell Laboratory.
   Report No.: AERE-G-3598. 1985.
   The EIX process for radioactive waste treatment.
   Turner. A D; Bridger, N J; Jones, C P; Neville, M D; Junkinson, A R. AEA Industrial Laboratory, B429, Harwell Laboratory, Oxfordshire, OXI 110RA, UK.
   Report No.: CONF-9509139. 1991.
2. The First Industrial HLW Partitioning Installation In Russia Is Operational.
   Post-Soviet Nuclear & Defense Mvonitor,
   Exchange/Monitor Publications, Inc. 29/08/96.
3. Radioactive waste treatment: Russian/US partnership in Research and Development.
   Fryberger, T B; Romanovskiy, V; Esimantovskiy, V; Lazarev, L; Albert. T; Hunter, T.
4. Synthesis of Cobalt Dicarbollide derivatives for addition and condensation polymerization.
   Balaich. G J; Miller, R L; Abney, K D.
   Book of Abstracts, 211th ACS National Meeting, New Orleans, La.
   March 24–28 (1996), INOR-390; Publisher: American Chemical Society.
5. SU-A-1603552, SU-A-1589858 and SU-A-1432953.
6. Isotachophoretic determination of chloro derivatives of Cobaltocarborane without the use of reference analytes.
   Simunicova, E; Kaniansky, D.
   J. Chromatogr. 390(1), p121–32. 1987.
7. New Synthetic Routes to B-Halogenated Derivatives of Cobalt Dicarbollide.
   Hurlburt. P K; Miller, R L; Abney, K D; Foreman, T M; Butcher, R J;
   Kinkead, S.
   Chemical sciences and technology division, Los Alamos National Laboratory, Los Alamos, N.M.
   Inorganic Chemistry 1995, 34, p5215–5219. 18/11/1994.
8. Synthesis and properties of Cobalt complexes containing the bidentate pi-bonding $B_8C_2H_{10}^{-4}$ ligand.
   Francis. J N; Hawthorne, M F.
   Inorganic Chemistry 1971, 10 (4) p863-64. US Government Research And Development Report, 70 (2) p54. 318/1970.
9. Preparation and crystallographic characterisation of the $(B_9C_2H_{11}$—Co—$B_8C_2H_{10}$—Co—$B_8C_2H_{10}$—Co—$B_9C_2H_{11}(-3))$ anions: a system with four fused icosahedra.
   Churchill M R; Reis, A H. Francis, J N; Hawthorne M F.
   Journal Of The American Chemical Society, 90. p1663,
   Inorganic Chemistry,. 8, p2080. Clair, D S; Zalkin, A; Templeton, D H. 26/3/1970.
10. Synthesis and properties of polynuclear cobalt (III) complexes containing dicarbollide(2-) and dicarbacanastide(4-) anions.
    Volkov, O V; Voronina. G S; Volkov. V V.
    Institute of Inorganic Chemistry, Siberian Branch Of The Russian Academy Of Sciences.
11. New series of organoboranes III. Some reactions of 1,2 Dicarbaclovo-dodecaborane(12) and its derivatives.
    Heying, T L; Ager, J W; Clark, S L; Alexander, R P; Papetti. S; Reid, J A;
    Trotz, S I.
    Inorganic Chemistry, P1096–1107. Schroeder, H; Heying, T L,. Reiner, J R. 14/6/1993.
12. Cobalt Dicarbollide containing polymer resins for caesium and strontium uptake.
    Steckle, W P Jr. Duke. J R Jr; Jorgensen, B S.
    Polymer and Coatings Group, Los Alamos National Laboratory, Los Alamos. New Mexico, 87504, USA.
    Polym. Mater. Sc. Eng., 71, P507-8, 1994.
13. New routes to C-substituted derivatives of cobalt dicarbollide.
    Miller, R L; Scott B L; Melo, M M; Abney, K D; Balaich G J.
    Book of Abstracts, 211th ACS National Meeting, New Orleans. La. March 24–28 (1996). INOR-296; Publisher: American Chemical Society.
14. B-halogenation derivatives of the bis(1,2-dicarbollyl) cobalt (III) anion.
    Matel, L; Macasek. F Rajec, P: Hermaiiek, S; Plesek, J. Polyhedron. Vol 1 No. 6, P511–519, 1982.

What is claimed is:

1. An electrochemical ion exchange flow through cell, characterised in that it comprises a metal carbollide as ion exchange material.

2. A cell of claim 1, wherein the metal carbollide is a metal ortho dicarbollide.

3. A cell of claim 1, wherein the metal carbollide is a cobalt carbollide.

4. A cell of claim 1, wherein the metal carbollide is polynuclear.

5. A cell of claim 4, wherein the metal carbollide is trinuclear.

6. A cell of claim 1, wherein the metal carbollide comprises a substituted carbollide cage.

7. A cell of claim 6, wherein the carbollide is substituted by halogen.

8. A cell of claim 7, wherein the halogen is chlorine.

9. A cell of claim 7, wherein the halogen atom(s) is/are bonded to boron.

10. A cell. of claim 9 wherein the carbollide is the dodecachloro cobalt carbollide trimer $[C_2B_9H_8Cl_3—Co—C_2B_8H_7Cl_3—Co-C_2B_8H_7Cl_3—Co—C_2B_9H_8Cl_3]^{3-}$.

11. A cell of claim 6, wherein the carbollide cage is in the form of an organic polymer.

12. A cell of claim 1, wherein the carbollide is substituted by an organic moiety.

13. A cell of claim 12, wherein the carbollide is substituted by an organic moiety comprising a thiol group or a carboxyl group.

14. A cell of claim 13, wherein the organic moiety is attached to a carbon site of the carbollide cage to which it is bonded and is of the formula $$—R^1—(Ar)_m—(R^2)_n—X,$$

wherein Ar is an aromatic group, m and n are each independently 0 or 1, $R^1$ and $R^2$ are each independently an alkylene group and X is COOH or SH.

15. A cell of claim 13, wherein the thiol group or carboxyl group is bound to the working electrode of the cell.

16. A cell of any of claim 1, wherein the metal carbollide is bonded to a resin.

17. A cell of any of the preceding claims and comprising:
    a housing having defined therein a chamber;
    a working electrode disposed within the chamber and associated with the metal carbollide ion exchange material; and
    a counter electrode juxtaposed to an exposed surface of the ion exchange material.

18. An electrochemical ion exchange (EIX) process for removing from an aqueous medium dissolved cations extractable using a metal carbollide, which process comprises:

providing an EIX flow through cell having a cathode comprising a metal carbollide as ion exchange material;

applying a negative potential to the cathode;

passing the aqueous medium through the through flow cell; then passing a flush liquid into or through the flow through cell and, whilst the flush liquid is in the flow through cell, applying a positive potential to the cathode to cause adsorbed cations to elute into the flush liquid.

19. A process of claim 18, wherein the cations comprise strontium ions or caesium ions, or both.

20. A process of claim 18 wherein the metal carbollide is a metal ortho dicarbollide.

21. A metal carbollide, characterised in that it comprises carbollide cages, substituted by an organic moiety selected from carboxylic acids and thiols.

22. A metal carbollide according to claim 21, wherein the metal carbollide is polynuclear.

23. A metal carbollide of claim 21, wherein the carbollide cages are ortho dicarbollides.

24. A metal carbollide of claim 21 wherein the metal is cobalt.

25. A metal carbollide of claim 21, wherein all the carbollide cages are substituted.

26. A metal carbollide of claim 21 which is trinuclear.

27. A method for making a cation exchanger electrode to be stable at both acid and basic pH, comprising embedding a wire or mesh in a polynuclear metal carbollide or in a halogenated metal carbollide of claim 26.

28. A metal carbollide of claim 21 wherein the organic moiety is attached to a carbon site of the carbollide cage to which it is bonded and is of the formula $$—R^1—(Ar)_m—(R^2)_n—X,$$

wherein Ar is an aromatic group, m and n are each independently 0 or 1, $R^1$ and $R^2$ are each independently an alkylene group and X is COOH or SH, the COOH optionally being in the form of a reactive derivative thereof.

29. A metal carbollide of claim 28, wherein the total number of in-chain alkylenic carbon atoms is at least 3 and optionally no more than 20.

30. A metal carbollide of any of claim 21 wherein the carboxyl or thiol group is bonded to a metal wire or mesh.

* * * * *

UNITED STATES PATENT AND TRADEMARK OFFICE
CERTIFICATE OF CORRECTION

PATENT NO. : 6,423,199 B1                                                                                   Page 1 of 1
DATED       : July 23, 2002
INVENTOR(S) : Tinker et al.

It is certified that error appears in the above-identified patent and that said Letters Patent is hereby corrected as shown below:

Column 4,
Line 57, the following paragraph should be inserted:
--       The invention also provides a cation exchanger electrode comprising a metal carbollide, as well as an EIX process for removing dissolved cations from an aqueous medium which uses a cell of the invention. --

Column 16,
Line 44, should read as follows: -- 30. A metal carbollide of claim 21 wherein the --

Signed and Sealed this

Twenty-second Day of April, 2003

JAMES E. ROGAN
*Director of the United States Patent and Trademark Office*